United States Patent [19]

Webb et al.

[11] Patent Number: 4,768,874
[45] Date of Patent: Sep. 6, 1988

[54] SCANNING OPTICAL APPARATUS AND METHOD

[75] Inventors: Robert H. Webb, Lincoln, Mass.; Douglas P. Wornson, Northfield, Minn.

[73] Assignee: Eye Research Institute of Retina Foundation, Boston, Mass.

[21] Appl. No.: 95,307

[22] Filed: Sep. 10, 1987

[51] Int. Cl.$^4$ .............................................. A61B 3/14
[52] U.S. Cl. ..................................... 351/206; 351/221
[58] Field of Search ....................... 351/206, 207, 221; 354/62

[56] References Cited

U.S. PATENT DOCUMENTS 4,213,678  7/1980  Pomerantzeff et al. ............ 351/206
4,579,430  4/1986  Bille .................................... 351/206

Primary Examiner—Rodney B. Bovernick
Assistant Examiner—P. M. Dzierzynski
Attorney, Agent, or Firm—Lahive & Cockfield

[57] ABSTRACT

An optical apparatus for providing a two-dimensional output representation of reflection characteristics of an eye fundus in which a laser beam is passed through an anamorphic optical element to produce an output beam focused on a first axis and dispersed on a second axis normal to the first axis forming a line. The line of the output beam is directed onto a scanning element which moves the beam along the first axis and a focusing element directing the output beam from the scanning element through the pupil of the eye onto the fundus, the size of the beam being such that it has a small cross sectional area at the pupillary plane of the eye compared to the diameter of the pupil. The light from the fundus is reflected back through an exit aperture which is large compared to the cross sectional dimension of the input beam at the pupillary plane. The device includes a detector which extends along the non-scanning coordinate of the scanned area. A beam separating means separates the input laser beam from the reflected output beam which is directed toward the detector positioned at a retinal conjugate of the eye. Signal processing means processes the signals received at the detector to provide the two-dimensional output representation.

13 Claims, 3 Drawing Sheets

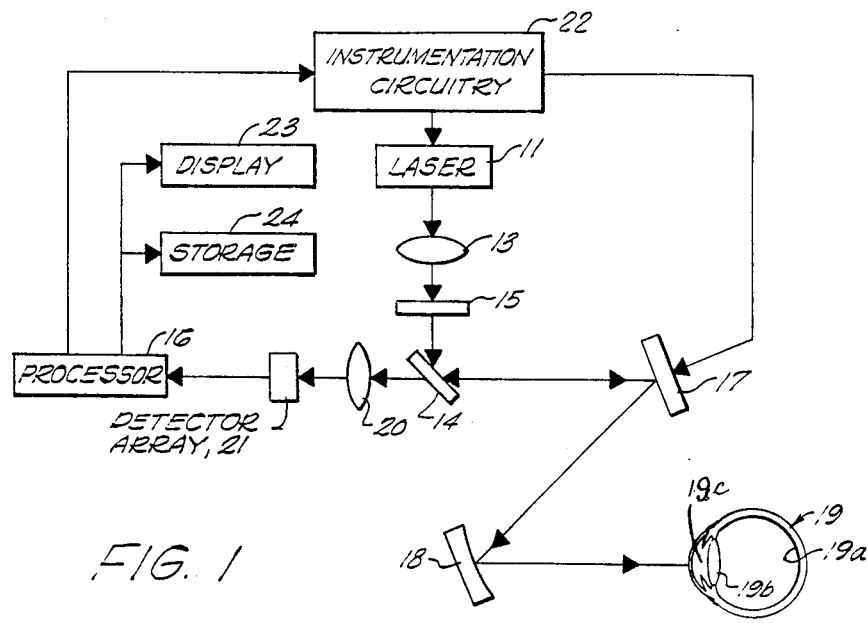
FIG. 1
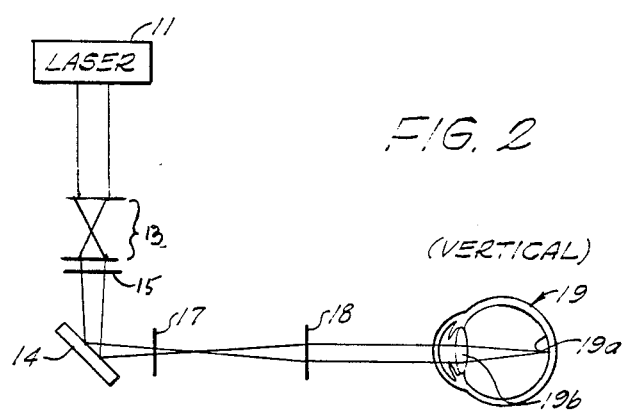
FIG. 2 (VERTICAL)
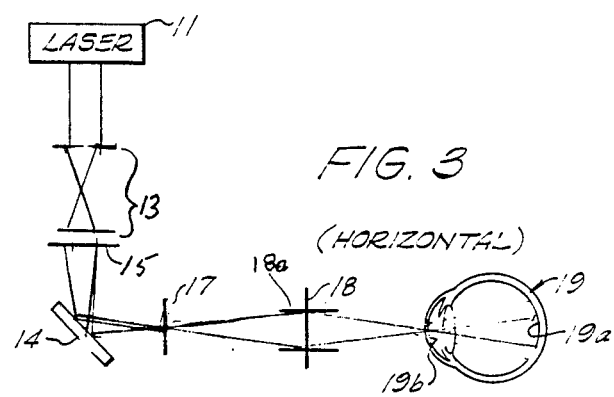
FIG. 3 (HORIZONTAL)

SCANNING OPTICAL APPARATUS AND METHOD

FIELD OF THE INVENTION

This invention relates in general to optical instruments and methods, and more particularly to an instrument for scanning a surface or other structure with an optical beam, detecting the light emitted from the structure, and generating either a two-dimensional representation of an image of the structure or a set of stored data representing such an image.

BACKGROUND OF THE INVENTION

In the art of optical instruments, it is known to scan a surface to be imaged with a small light source, collect the light reflected from the illuminated spot and direct it to a detector which provides an output signal varying in time in correlation with the scanning of the illuminated spot across the surface. The detector output can be stored in a permanent storage medium or provided directly to a scanning display device, such as a television raster or a cathode ray tube display. By synchronizing the scanning operation of the illuminating source with the scanning of the display signals, a two dimensional image is produced.

One such instrument is a scanning ophthalmoscope which produces an image of the fundus of the eye. It has been found that the use of a laser light source provides improved imaging in an ophthalmoscope. A laser scanning ophthalmoscope is described in U.S. Pat. No. 4,213,678.

In a device as described in the noted patent, the entrance pupil for the scanning laser beam has a small cross sectional area within the pupil of the eye, typically 0.8 mm in diameter, whereas the exit aperture for the reflected light is the overall pupil of the eye, which typically is nine mm in diameter. The detector is placed in a plane conjugate to this exit aperture.

An improved technique is described in pending U.S. application Ser. No. 876,230 filed June 19, 1986 and U.S. application Ser. No. 876,231 filed June 19, 1986.

SUMMARY OF THE INVENTION

Broadly speaking, in the present invention a confocal scanning ophthalmoscope which scans along only one coordinate is constructed utilizing a laser source, an asymmetrical focusing element, such as a cylindrical lens, together with a deflection galvanometer or other scanning element for scanning on the same axis for which the asymmetrical element focuses. The laser beam which is of generally circular cross section and small compared to the diameter of an eye pupil is directed onto the cylindrical lens, which focuses on the vertical axis but does not focus along the horizontal axis so that what is produced at the focal point of the cylindrical lens is a vertically focused horizontal extended rectangular beam characterized by a low vertical to horizontal aspect ratio. In other words it appears to be a horizontal line beam. This beam is directed by a small turning mirror onto a deflection galvanometer or other vertical scanning means which scans it along a vertical coordinate. The scanning beam is directed by means of another focusing element, preferably a mirror, through the eye pupil and onto the fundus of the eye, the focal length being arranged such that the beam as it passes through the pupil is focused to a narrow waist, substantially smaller than the diameter of the eye pupil, and then expands back to the width of the horizontal beam for scanning the fundus. The overall input beam system then scans the line beam vertically over the fundus, thereby scanning an area of the fundus.

The light reflected from the area of the fundus illuminated by the beam is collected by the focusing mirror and directed back to the vertical deflection mirror, which is positioned so that its face is approximately conjugate with the plane of the eye pupil. The turning mirror is placed in the center of the reflected beam and since its diameter is very small compared to the cross sectional area of the beam as it leaves the galvanometer mirror, it intercepts only a very small portion of the reflected light. The major portion of this reflected output beam then passes by the turning mirror to a lens placed at the pupillary conjugate which focuses it onto a horizontally distributed line of detectors located at a retinal conjugate plane. The detectors produce a plurality of electrical signals representing the time variation of light arriving at each one of the horizontally distributed detectors. This electrical signal can then be used to develop a raster display or for optical pattern recognition.

DESCRIPTION OF THE DRAWINGS

In the drawings:
FIG. 1 is a diagrammatic representation of one embodiment of a scanning instrument according to the principles of this invention;
FIGS. 2 and 3 are explanatory ray diagrams of optical beam features of the embodiment illustrated in FIG. 1.

DESCRIPTION OF THE PREFERRED EMBODIMENTS

Figure 4:
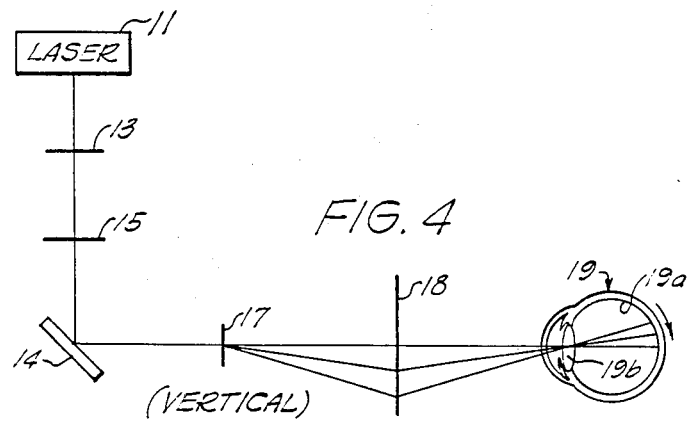
FIG. 4 is an explanatory ray diagram of optical scan features of the embodiment of FIG. 1.

FIG. 1 shows an embodiment of the invention in the form of an ophthalmoscope. A laser illumination source 11 produces a narrow incident light beam which passes through an anamorphic beam shaping system 13, 15 which produces a beam focused along a first axis and diverging along an axis normal to the first axis. This beam, in turn, impinges on a small turning mirror 14. The mirror 14 directs the incident laser beam onto the reflecting surface of a galvanometer deflection scanner 17 to produce a vertical scanning motion. From the galvanometer deflection scanner 17, the laser input beam is directed onto a focusing mirror 18, for conjugating the galvanometer 17 to the pupil 19c. The incident beam also passed through the crystalline lens of the eye 19b.

The reflected light from the fundus 19a is directed back over a common portion of the foregoing optical input path, which includes focusing mirror 18, and vertical scanner 17. Both of these common elements can be mirrors and hence do not contribute reflections of the input beam back to the detector as noise background. The reflected output beam from the scanner 17 in large part passes by the turning mirror and hence separates from further traverse along the input optical path. Instead the output beam is directed through focusing lens 20 onto an optical detector array 21.

The detector 21 is electrically connected to an electrical instrumentation unit 22 which provides electrical control signals to the laser source 11 and electrical drive signals to the scanning deflection element 17. In essence, the instrumentation unit provides synchronization of the signals received at the scanning element 17 so that the temporal order of the signals produced by the detector 21 can be correlated with the location of the scanned incident laser beam on the surface of the fundus. The detector 21 is a multi-element detector having discrete detection elements dispersed along the horizontal axis. It responds to incident light by providing from each discrete horizontal element a time varying electrical signal. These signals are provided to a signal processor 16, which processes the data representing simultaneous reflections from a horizontally extended beam correlated with the variation in time as that beam is scanned vertically to produce signals suitable for creating a raster display. The control and synchronization which the processor and instrumentation unit provide enables a display device 23, such as a television raster device, to form a two-dimensional display of an image of the eye fundus 19a, in response to the reflected optical energy it receives. The detector signal may be applied to a long term storage element 24, such as a video tape recorder, for subsequent readout and display. Alternatively the output signal may be compared to predetermined patterns of signal for eye identification, disease screening or the like. These patterns may be stored time varying signals from specific detector locations. For a description of a suitable electrical timing and control circuit, reference is made to U.S. Pat. No. 4,213,678 which is incorporated herein by reference. If the detector is a charge coupled detector, it may integrate for only 63 microseconds. This requires different, but well understood, timing circuitry.

THE LASER GENERATOR

The laser 11 can be any suitable laser light source which provides emission at frequencies yielding appropriate contrast for the fundus, or other target. Typically, the laser 11 is an Argon-Krypton laser or Helium-Neon laser operated at a power level to produce an illumination irradiance of one hundred microwatts per square centimeter or substantially less at the fundus. The laser 11 may also be selected to emit in the infrared wavelength region to provide a scanning beam which is not perceptible to the subject. For these irradiances the eye pupil need not be medically dilated to obtain an imaqe of the fundus. For color imaging two lasers of different wavelengths may be employed and converted into a single beam with a dichroic beam splitter.

THE INPUT OPTICAL SYSTEM

The purpose of the input optical system is to scan the fundus along a first axis with a rectangular optical beam having a low "height to width" aspect ratio to illuminate a "vertical" sequence of these line-like rectangular areas across the fundus surface in a known pattern so that the reflected light detected in time sequence can be electrically converted to a two-dimensional representation of the reflection characteristics of the fundus. Of course the first axis could be horizontal so that it would be the "width to height" aspect ratio which would be low. In one illustrative instrument, the input optical sytem forms the incident laser beam with a cross sectional area of substantially 0.9 mm diameter at the entrance pupil of the eye and focused on the fundus to produce an illuminated segment approximately twelve microns by 6 mm.

The vertical scanning motion in the illustrated preferred embodiment is introduced by a deflection galvanometer 17 that provides a scan action which corresponds with the television vertical scan of 60 Hz. Galvanometer controls, such as those manufactured by General Scanning of Watertown, Mass., are suitable for driving and controlling the position of th galvanometer mirror. The mirror 17 can, for example, be a type G120D or G325D General Scanning mirror. The deflection galvanometer could be replaced by a slow rotating polygon.

The shaped laser beam must be in (vertical) focus at the retina, and the scan waist must be located (approximately) at the pupil of the eye. Under these circumstances the beam cross section on the retina is appropriate for the available resolution, and the image will appear in focus at the TV screen even if it is not in focus at the confocal aperture. It is the focus of the incident beam which determines the picture's resolution and the focus of the return beam (at the confocal stop) which controls contrast. The system, however, is confocal only in the scanning (vertical) dimension, hence the statement applies only to that dimension. The fact that these controls are largely orthongonal is what allows flexibility as to mode of view.

The turning mirror 14 preferably is a stationary mirror reflector. It is small in size in order to produce a minimal shadow in the output beam, and hence preferably is only large enough to intercept the input beam which the focusing element 13 and cylindrical lens 15 direct, via the turning mirror, to the scanner 17. In the configuration shown the turning mirror acts as the beam separator between the input and reflected return beam.

FIGS. 2 and 3 illustrate features of the input optical system. FIG. 2 represents the vertical aspect of the input beam with the scanner 17 assumed to be stationary in a neutral, non-deflecting, position. The narrow collimated incident beam from the laser is shaped by lens 13 and directed onto cylindrical lens 15. The cylindrical lens is positioned such that it focuses on the vertical axis (which is the axis illustrated in FIG. 2). The focused beam from the cylindrical lens 15 is then reflected from turning mirror 14 onto deflecting galvanometer mirror 17 which directs it onto the face of relay mirror 18 which focuses the cross sectional beam on the retina 19a of the eye 19. It will be understood that, while the scanning axis is the vertical axis and the extended beam from the cylindrical lens is horizontal, this is an arbitrary choice, and the system could be arranged in the opposite fashion.

FIG. 3 is again a beam diagram of the same optical configuration as FIG. 2, representing however the view along the horizontal axis. Thus, along this axis, the beam from the cylindrical lens 15 is focused on the galvanometer reflecting surface 17 and on the pupil of the eye. (Thus, while in FIG. 2, the foci are at the optical conjugates of the retina, in FIG. 3 they are at the conjugates of the pupil.) The turning mirror 14 which is small compared to the pupil of the eye, typically being less than 0.9 mm, is positioned sufficiently close to the cylindrical lens so that the horizontal extension of the beam location of the turning mirror is not greater than the dimension of that mirror. What is reflected from the turning mirror 14 is then, in the horizontal dimension, an extended line which is in turn focused by the relay mirror 18 onto the eye's pupil 19c. It spreads into a line at the retina. The beam cross section as it arrives at the retina has a generally rectangular shape with a very low aspect ratio of vertical dimension to horizontal dimension (a horizontal line). This horizontal line beam is scanned in a vertical direction over the retina surface by the action of the deflecting galvanometer mirror 17. Since the line at the retina may have a gaussian profile, it will be necessary to put in a stop at 18a to give it crisper ends.

FIG. 4 which represents scan features of the input system, illustrates the input beam instantaneously as a single ray which the scanning element moves in the vertical direction as a function of time. The drawing shows, in effect, the time exposure on the vertical axis which, for the scanned input beam includes the entrance pupil. The scan angle is the full angle of this envelope in the plane of the scan.

The mirror 18 is spherical and large so that even at f/2 (for the scan) the eye's pupil is far back from the optics. With human subjects there are some inflexible dimensions. The mirror is spherical because no aspheric is correct for both beam and scan systems at all points. That constraint can be understood by noting that the beam on one side of this mirror may be always collimated, no matter where it hits the mirror. So the mirror must have everywhere the same local curvature-which implies a sphere.

THE OUTPUT OPTICAL SYSTEM

As described, a major portion of the output optical system has a common optical path with the input system. This common path includes both the scanning element 17 and the focusing mirror 18. In the output system light reflected from the galvanometer mirror 17 passes around the turning mirror 14 and is incident on the detector system which includes lens 20 and detector 21.

Figure 5:
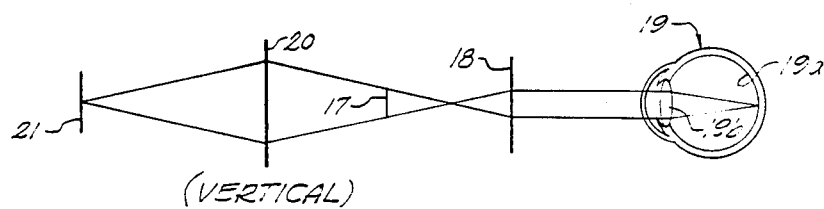
FIGS. 5 and 6 are also explanatory ray diagrams of optical beam features of the invention illustrated in FIG. 1.
Figure 6:
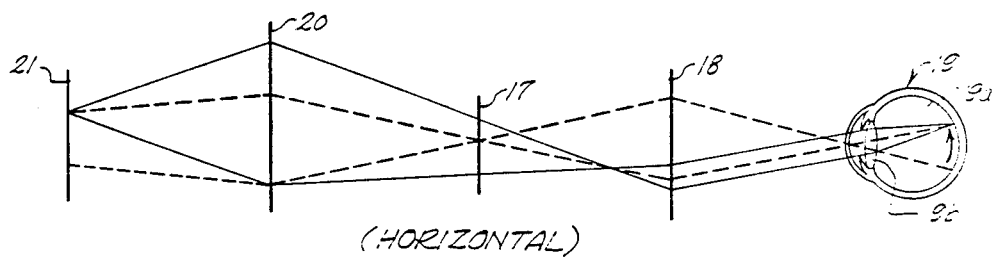

FIG. 5 represents the output beam along the vertical axis in the same manner as the representation in FIG. 2, while FIG. 6 represents that same output beam along the horizontal axis in the same manner as FIG. 3.

As illustrated in FIG. 5, the reflected beam from the fundus has an exit aperture large compared to the vertical dimension of the scanning beam, preferably substantially the entire pupil of the eye, with a diameter of as much as nine mm. The image of this aperture at its conjugate plane also is nine mm. Absent magnification, the reflected output beam from the illuminated area on the fundus likewise is approximately nine mm in diameter at any conjugate of the exit pupil, which is where the scan element 17 is located.

In this configuration the central region of the eye's pupil is used as an entrance pupil and the remaining annulus an exit pupil, thus conforming to Gulstrand's principle. This means that scanner 17, optically conjugate to the pupil, needs to be big enough to intercept that larger return beam. For the vertical scanner which moves as a 60 Hz sawtooth, a 10-15 mm mirror is suitable.

The ophthalmoscope can have a small entrance pupil, as described above, due to the large radiance of the incident beam. The output beam, however, has relatively low radiance, and hence the provision of this large output pupil is desired to collect a maximal amount of output light energy. The large exit aperture hence enhances the high efficiency of the instrument. It also facilitates viewing a large portion of the eye fundus.

FIG. 5 also illustrates, with exaggerated scale, that the output beam passes around the turning mirror 14, which hence casts a small shadow generally of low significance.

It is desirable to separate the incident and return beams as close to the scanning mirror as possible in order to place the incident beam in the center of the return beam and thus stop direct reflection from the cornea (and spectacles if desired) from reaching the detector.

FIG. 6 illustrates the reflected beam from the fundus along its horizontal axis. In both figures the field lens 20 is placed at the pupillary conjugate plane while the detector 21 is placed at a retinal conjugate plane. Thus the image of the retina at the plane of the detector 21 is the portion of the illuminated area which at any instant in time has an extended width and a very low height. An ideal detector 21 is then an array of very small discrete elements dispersed horizontally and having a low vertical height. One suitable detector for this configuration is a series of charged coupled detectors providing, for example, 512 discrete horizontal elements. The output signals are then taken in parallel from each of the elements. The time variance at each element represents the change in the retinal image as the line of illumination is scanned in the vertical direction. The output electrical signals can be transmitted to a processor 16 which can transfer the processed information into a storage unit 24, to a display 23, which would typically be a television raster, or to further pattern recognition means.

Figure 7:
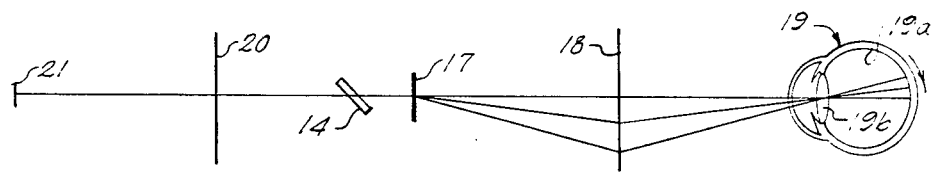
FIG. 7 is an explanatory ray diagram of the reflected optical beam of the embodiment illustrated in FIG. 1.

FIG. 7 is a ray diagram of the scanning envelope of vertical dimension of the output reflected beam.

Although specific block diagrams have not been provided for the circuitry components and for the process and logic, it is believed that synchronizing the raster scan with the galvanometer mirror oscillation and the processing of the time variant signals to produce a raster scan is well known to those skilled in the art. Reference is also made to copending U.S. application Ser. No. 876,230, which is incorporated herein by reference.

The system described herein has many of the advantages of a double scanning confocal ophthalmoscope. It is confocal in one dimension, and has the advantage of using the identical optical path for the reflected beam, which is descanned at the reflecting galvanometer mirror. The positioning of the turning mirror as a small centrally located mirror in the reflected beam provides that very little light intensity is lost and that corneal reflections are blocked. Since the contrast enhancement is in the ratio of observed to illuminated retina, this system improves contrast by 512, while a fully double scanning optimum improves it by $(512)^2$. One clear advantage of the system as illustrated is the simplicity and cost effectiveness resulting from including only one scanning element.

Figure 8:
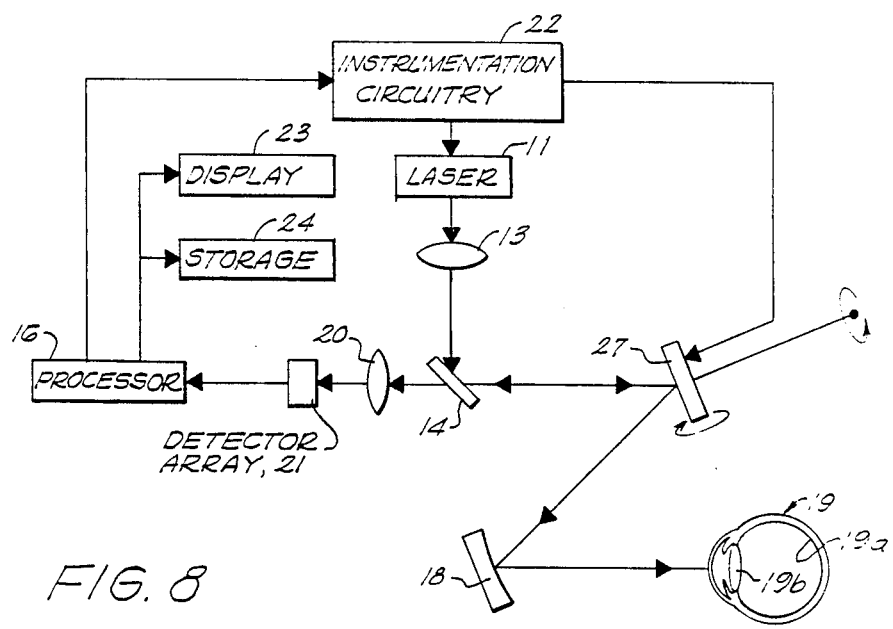
FIG. 8 is a diagrammatic illustration of a second embodiment of an optical instrument constructed in accordance with the principles of this invention.

While the embodiments as described have generated a rectangular raster scan, it is possible by employing a rotational optical element to generate a polar scan rather than a vertical deflection. Thus, in a configuration is shown in FIG. 8 in which the vertical galvanometer is replaced with a dove prism or a Dove mirror (the mirror analogue of a Dove prism) which is rotated at a predetermined speed to produce at the retina, a polar scanning line shaped beam and, at the output detector, a signal which varies in time in accordance with the polar scan.

While the system has been described in terms of presenting a visual image of the fundus. The apparatus has other uses, for example, for eye recognition, the detected information in either the polar scan or the rectilinear scan configuration can be matched against previously recorded information for an individual retina, thus providing determination of the identity or lack of identity of the person. Similarly, patients can be screened to determine whether there are specific characteristics of the retina indicating broad categories of disease, or change of condition. In these applications information developed by the detector and processor would be either visually screened or processed electronically to determine whether specific areas of the retina are characterized by specific images or changes in images.

Other embodiments of the invention including modifications of and deletions from these disclosed embodiments will accordingly be apparent to those skilled in the art.

What is claimed as new and secured by Letters Patent is:

1. An optical apparatus for providing a two-dimensional output representation of reflection characteristics of an eye fundus, said apparatus comprising,
    a laser source for generating a laser beam of defined symmetrical cross sectional area which is small compared to an area of the fundus to be scanned,
    an optical system for directing said laser beam through the pupil of the eye onto said fundus area, and for directing light reflected from the portion of said fundus area illuminated by said laser beam, onto a detector, said optical system including,
        an anamorphic optical element positioned to produce an output beam focused on a first axis and dispersed on a second axis normal to said first axis, forming a line at the focal point,
        a scanning element positioned to receive said anamorphic element output beam and move said beam along said first axis to scan said beam on a first coordinate across an area of said fundus,
        a fucusing element for directing said anamorphic element output beam from said scanning element through the eye pupil onto the fundus area, such that said beam passes through the plane of the pupil of the eye and has at that plane a small cross sectional area compared to the diameter of the pupil, said focusing element being positioned to produce at said scanning element a conjugate image of said eye pupil,
        an exit aperture for reflected light from said fundus area illuminated by said beam, said exit aperture being large compared to the cross sectional dimension of said input beam at said pupillary plane,
    a detector means for generating a signal varying in time with variation in the amount of light received by it, said detector means including a series of discrete detector elements extending along one coordinate such that it provides in each discrete element a time varying signal corresponding to the variations in time of the amount of light received by that element,
    beam separating means positioned to direct the anamorphic element output beam toward said scanning element and to direct the reflected light from said scanned fundus area toward said detector, said detector being positioned at a retinal conjugate of said eye and said coordinate along which said discrete detector elements extend being aligned with the extended axis of said anamorphic element output beam on said fundus, and
    signal processing means for processing said time varying signals from said discrete elements to provide from said signals said two dimensional output representation of the reflection characteristics of said eye fundus.

2. Apparatus in accordance with claim 1 wherein said anamorphic element is a cylindrical lens.

3. Apparatus in accordance with claim 1 wherein said beam separating mirror is a turning mirror, the diameter of said turning mirror being just sufficient to accommodate the cross sectional area of said laser beam.

4. Apparatus in accordance with claim 1 wherein said scanning element is a deflection galvanometer.

5. Apparatus in accordance with claim 1 wherein said focusing element directs said anamorphic optical element output laser beam through the plane of the pupil of the eye at approximately the center of that plane.

6. Apparatus in accordance with claim 1 wherein said detector means is an array of charge-coupled detectors.

7. Apparatus in accordance with claim 1 wherein said signal processing means includes data processing means for comparing the pattern in time and location of said signals received by said detector to a predetermined pattern of time and location for said signals.

8. Apparatus in accordance with claim 1 wherein said signal processing means correlates said time varying detector signals with the motion of said scanning element to provide a descanned output signal.

9. Apparatus in accordance with claim 1 wherein said scanning means scans said anamorphic element output laser beam on said eye fundus in a rotational pattern.

10. Apparatus in accordance with claim 9 wherein said scanning means is a rotating Dove mirror.

11. An apparatus in accordance with claim 1 and further including a display means for providing a two-dimensional representation of said eye fundus in response to said processed detector signals.

12. Apparatus in accordance with claim 11 wherein said scanning means scans said anamorphic element output laser beam on said eye fundus in a rotational pattern.

13. Apparatus in accordance with claim 2 wherein said display means is a television raster display.

* * * * *